United States Patent
Lee

(10) Patent No.: US 9,885,679 B2
(45) Date of Patent: Feb. 6, 2018

(54) DETECTING DEVICE AND DETECTING METHOD FOR DETECTING A USAGE STATE OF A SOCKET

(71) Applicant: POWERTECH INDUSTRIAL CO., LTD., New Taipei (TW)

(72) Inventor: Yu-Lung Lee, New Taipei (TW)

(73) Assignee: POWERTECH INDUSTRIAL CO., LTD., New Taipei (TW)

(*) Notice: Subject to any disclaimer, the term of this patent is extended or adjusted under 35 U.S.C. 154(b) by 60 days.

(21) Appl. No.: 15/186,398

(22) Filed: Jun. 17, 2016

(65) Prior Publication Data

US 2017/0299535 A1    Oct. 19, 2017

(30) Foreign Application Priority Data

Apr. 15, 2016   (TW) .............................. 105111835 A

(51) Int. Cl.

| | | |
|---|---|---|
| *G01N 27/04* | (2006.01) | |
| *G01R 27/20* | (2006.01) | |
| *G01R 31/28* | (2006.01) | |
| *G01R 31/04* | (2006.01) | |
| G01R 1/04 | (2006.01) | |
| G01R 17/10 | (2006.01) | |

(52) U.S. Cl.
CPC ......... *G01N 27/045* (2013.01); *G01R 27/205* (2013.01); *G01R 31/045* (2013.01); *G01R 31/2863* (2013.01); *G01R 1/0408* (2013.01); *G01R 17/105* (2013.01)

(58) Field of Classification Search
CPC ........ G01N 27/00; G01N 27/02; G01N 27/04; G01N 27/045; G01N 17/00; G01N 17/002; G01N 17/02; G01R 1/0408; G01R 1/0433; G01R 1/045; G01R 1/0483; G01R 1/067; G01R 17/105; G01R 27/00; G01R 27/08; G01R 27/14; G01R 27/20; G01R 27/205; G01R 31/024; G01R 31/045; G01R 31/2812; G01R 31/2813; G01R 31/2863; G01R 31/2886; G01R 31/3274; G01R 31/3278

USPC ....... 324/600, 649, 691, 693, 500, 512, 525, 324/537, 750.16, 756.01, 756.02

See application file for complete search history.

(56) References Cited

U.S. PATENT DOCUMENTS

| | | | | |
|---|---|---|---|---|
| 3,986,763 | A * | 10/1976 | Sparrow ............ | H01R 13/4534 439/137 |
| 5,003,486 | A * | 3/1991 | Hendel ................. | H01R 13/44 324/525 |
| 5,650,771 | A * | 7/1997 | Lee ........................ | G01R 15/12 340/538.17 |

(Continued)

*Primary Examiner* — Hoai-An D Nguyen
(74) *Attorney, Agent, or Firm* — Li & Cai Intellectual Property (USA) Office

(57) ABSTRACT

A detecting device for detecting a usage state of a socket includes a carrier, a movable assembly and a conductivity detecting module. The carrier has a first plug hole and a second plug hole. The movable assembly is movably disposed in the carrier. The conductivity detecting module is disposed on the carrier. The movable assembly is moved for exposing the first plug hole and the second plug hole by an external pushing force, and a detecting signal of the socket in-use is generated by the conductivity detecting module according to movement of the movable assembly.

11 Claims, 10 Drawing Sheets

(56) References Cited

U.S. PATENT DOCUMENTS

| | | | |
|---|---|---|---|
| 8,840,418 B2* | 9/2014 | Chien | H01R 13/6392 |
| | | | 439/270 |
| 9,450,325 B1* | 9/2016 | Lai | H01R 13/4534 |
| 2002/0195122 A1* | 12/2002 | Hembree | H01L 21/67028 |
| | | | 134/3 |
| 2004/0070275 A1* | 4/2004 | Niv | H02J 3/06 |
| | | | 307/39 |
| 2006/0039102 A1* | 2/2006 | Lai | H01R 13/7036 |
| | | | 361/641 |
| 2009/0149085 A1* | 6/2009 | Hachadorian | H01R 13/447 |
| | | | 439/736 |
| 2011/0089892 A1* | 4/2011 | Lin | H01M 2/1055 |
| | | | 320/107 |
| 2016/0047848 A1* | 2/2016 | Chang | G01R 21/133 |
| | | | 702/61 |
| 2017/0279214 A1* | 9/2017 | Lee | H01R 13/4538 |

* cited by examiner

DETECTING DEVICE AND DETECTING METHOD FOR DETECTING A USAGE STATE OF A SOCKET

BACKGROUND OF THE INVENTION

1. Field of the Invention

The present invention relates to a detecting device for detecting a usage state of a socket; in particular, to improve electrical safety by the conductivity detecting module of the detecting device.

2. Description of Related Art

Currently, the intelligent socket is used to detect whether the socked is in an in-use state at any time. However, this still needs an additional element and correspondingly complex mechanism, thus the intelligent socket is expensive and not universally used.

In view of this requirement, the instant invention provides a detecting device for detecting a usage state of a socket, which is not only for determining whether the socket is in-use using low cost manufacture, but also for improving electrical safety by preventing a foreign object from being inserted into the socket according to its improved structure.

SUMMARY OF THE INVENTION

The object of the instant invention is to solve the problems of the related art described above. The instant invention provides a detecting device for detecting a usage state of a socket.

An exemplary embodiment of the present disclosure provides a detecting device for detecting a usage state of a socket. The detecting device for detecting a usage state of a socket includes a carrier, a movable assembly and a conductivity detecting module. The carrier has a first plug hole and a second plug hole. The movable assembly is movably disposed in the carrier. The conductivity detecting module is disposed on the carrier. The movable assembly is moved for exposing the first plug hole and the second plug hole by the external pushing force, and a detecting signal of the socket in-use is generated by the conductivity detecting module according to movement of the movable assembly.

Another exemplary embodiment of the present disclosure provides a detecting method for detecting a usage state of a socket. The detecting method for detecting a usage state of a socket comprises the following steps. Providing the socket, the socket includes a carrier, a movable assembly movably disposed in the carrier and a conductivity detecting module disposed on the carrier. The carrier has a first plug hole and a second plug hole. Generating a detecting signal by the conductivity detecting module according to movement of the movable assembly. Determining whether the socket is in-use or not by a processing unit according to the detecting signal generated by the conductivity detecting module.

In sum, the advantages of the instant disclosure are to provide a detecting device for detecting a usage state of a socket, which detects whether the socket is in-use according relative movement of a movable assembly and a conductivity detecting module for improving electrical safety. In other words, the conductivity detecting module generates a detecting signal to terminal equipment according to movement of the movable assembly while a plug inserts into the socket, and reminds the user that the socket is in in-use state. Based on the detecting device, it prevents foreign objects being inserted into the socket and also monitors the socket usage state for improved socket safety.

In order to further understand the techniques, means and effects of the instant disclosure, the following detailed descriptions and appended drawings are hereby referred to, such that, and through which, the purposes, features and aspects of the instant disclosure can be thoroughly and concretely appreciated; however, the appended drawings are merely provided for reference and illustration, without any intention to be used for limiting the instant disclosure.

DETAILED DESCRIPTION OF THE PREFERRED EMBODIMENTS

Figure 1:
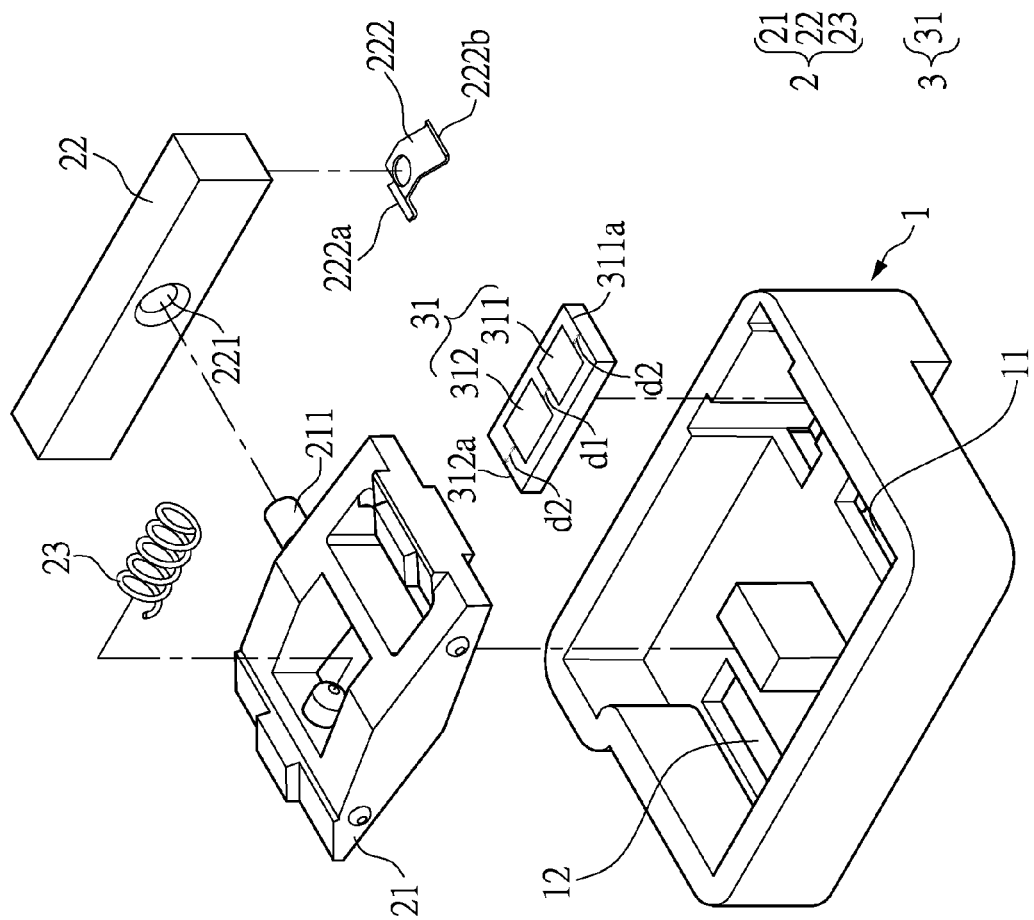
FIG. 1 shows a top perspective exploded view of the detecting device for detecting a usage state of a socket according to one of the embodiments of the instant disclosure.

Embodiments disclosed in the instant disclosure are illustrated via specific examples as follows, and people familiar in the art may easily understand the advantages and efficacies of the instant disclosure by disclosure of the specification. The instant disclosure may be implemented or applied by other different specific examples, and each of the details in the specification may be applied based on different views and may be modified and changed under the existence of the spirit of the instant disclosure. The figures in the instant disclosure are only for brief description, but they are not depicted according to actual size and do not reflect the actual size of the relevant structure. The following embodiments further illustrate related technologies of the instant disclosure in detail, but the scope of the instant disclosure is not limited herein.

Like reference numerals refer to like elements throughout. In the drawings, the dimensions and size of each structure are exaggerated, omitted, or schematically illustrated for convenience in description and clarity. It will be understood that although the terms of first, second, and third are used herein to describe various elements or signals, these elements or signals should not be limited by these terms. Terms are only used to distinguish one component from other components, or one signal from other signals. Therefore, a component referred to as a first component in one embodiment can be referred to as a second component in another embodiment. The terms of a singular form may include plural forms. In addition, the meaning of 'comprise', 'include', or 'have' specifies a property, a region, a fixed number, a step, a process, an element and/or a component but does not exclude other properties, regions, fixed numbers, steps, processes, elements and/or components.

Refer to FIG. 1. FIG. 1 shows a top perspective exploded view of the detecting device for detecting a usage state of a socket according to one of the embodiments of the instant disclosure. The embodiment provides a detecting device for detecting a usage state of a socket Z, which is used to detect whether the socket is in-use or not. The detecting device for detecting a usage state of a socket Z comprises a carrier 1, a movable assembly 2 and a conductivity detecting module 3. The carrier 1 has a first plug hole 11 and a second plug hole 12. The movable assembly 2 is movably disposed in the carrier 1. The conductivity detecting module 3 is disposed on the carrier 1. When the movable assembly 2 is moved for exposing the first plug hole 11 and the second plug hole 12 by an external pushing force, a detecting signal of the socket in-use is generated by the conductivity detecting module 3 due to movement of the movable assembly 2.

The first plug hole 11 of the carrier 1 is parallel to the second plug hole 12 of the carrier 1, and provides for two parallel blades of a plug to be inserted into the socket. Alternatively, the first plug hole 11 of the carrier 1 is perpendicular to the second plug hole 12 of the carrier 1, and provides for two perpendicular blades of a plug to be inserted into the socket. The shape or distance between the first plug hole 11 and the second plug hole 12 could be adjusted by those of ordinary skill in the art, and it is not limited herein.

The movable assembly 2 includes a movable member 21 and a connecting element 22. The movable member 21 is movably disposed in the carrier 1. A connecting column 211 of the movable member 21 is mated with the connecting hole 221 of the connecting element 22. An elastic element 23 is connected between the carrier 1 and the movable member 21 of the movable assembly 2. When the movable member 21 is moved and the elastic element 23 is deformed by the external pushing force, the first plug hole 11 and the second plug hole 12 are exposed by the movable member 21 and a detecting signal of the socket in-use is generated by the conductivity detecting module 3 according to movement of the connecting element 22. The elastic element 23 can be a spring or any element having elastic structure, and it is not limited herein.

The conductivity detecting module 3 is used for detecting whether the socket is in-use or not. The conductivity detecting module 3 has a signal generating unit. The signal generating unit generates a detecting signal to a processing unit (for example, a microcontroller or a microprocessor) by a movement of the movable assembly 2, and the processing unit determines whether the socket is in-use or not according to the detecting signal from the conductivity detecting module 3. In addition, no matter whether the conductivity detecting module 3 is disposed outside or inside the carrier 1, the conductivity detecting module 3 can correspond to the movable assembly 2 for detecting a movement of the movable assembly 2.

Figure 2:
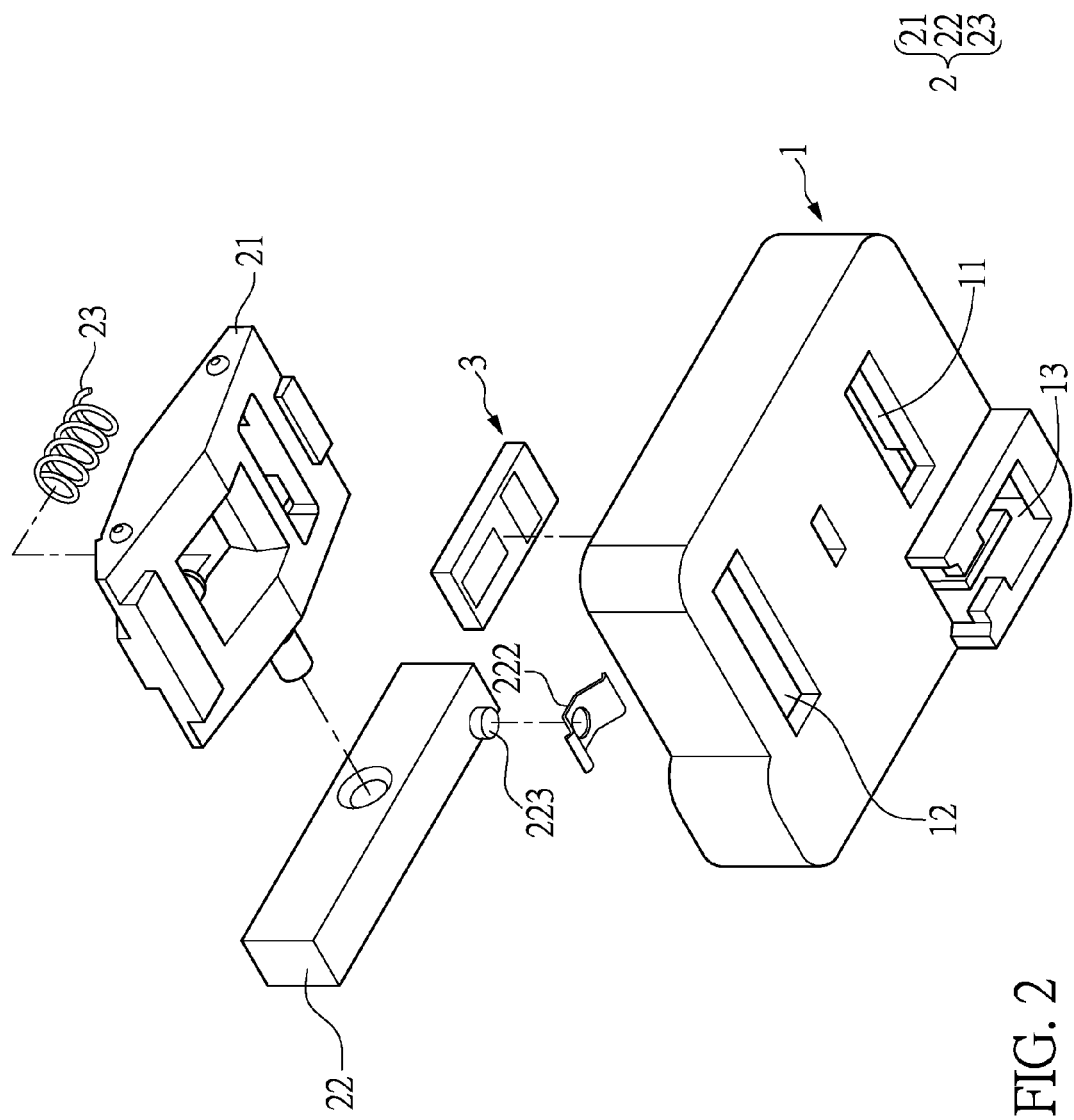
FIG. 2 shows a back perspective exploded view of the detecting device for detecting a usage state of a socket according to one of the embodiments of the instant disclosure.

Refer to FIG. 1 and FIG. 2. FIG. 2 shows a back perspective exploded view of the detecting device for detecting a usage state of a socket according to one of the embodiments of the instant disclosure. In this embodiment, the conductivity detecting module 3 is disposed in a mounting hole 13 on the carrier 1. The conductivity detecting module 3 further includes a circuit substrate 31 and at least one conductive pad 311, 312 is disposed on the circuit substrate 31. When a conductive sheet 222 disposed on the connecting element 22 is simultaneously electrically connected to the conductive pads 311, 312, the detecting signal of the socket in-use is generated by the circuit substrate 31.

A protrusion portion 223 of the connecting element 22 can mate with an opening of the conductive sheet 222. When the connecting element 22 is moved, it moves the conductive sheet 222. The conductive sheet 222 has a pair of pin portions 222a, 222b to form an arch bridge-like shape. Two the conductive pads 311, 312 of the circuit substrate 31 are disposed adjacent to each other. The pair of pin portions 222a, 222b of the conductive sheet 222 are respectively electrically connected to the two conductive pads 311, 312. In this embodiment, the first distance d1 between two the conductive pads 311, 312 is less than a second distance d2 between a lateral side 311a of the circuit substrate 31 to the conductive pad 311 and the other lateral side 312a of the circuit substrate 31 to the conductive pad 312, thus the conductive sheet 222 easily connects the conductive pads 311, 312, and the determining sensitivity is enhanced. Alternatively, the first distance d1 is larger than the second distance d2 or the first distance d1 is equal to the second distance d2, as it is not limited herein.

Figure 3:
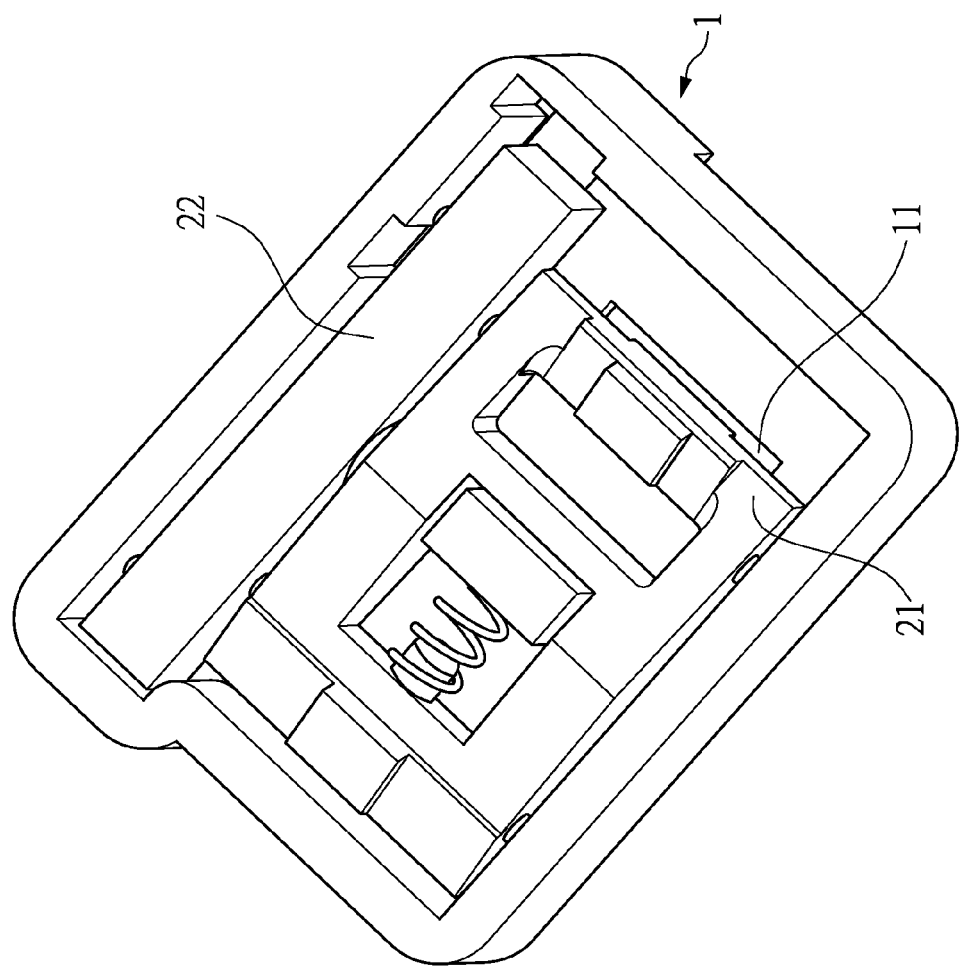
FIG. 3 shows a perspective assembly view of the detecting device in the non-use state according to one of the embodiments of the instant disclosure.
Figure 4:
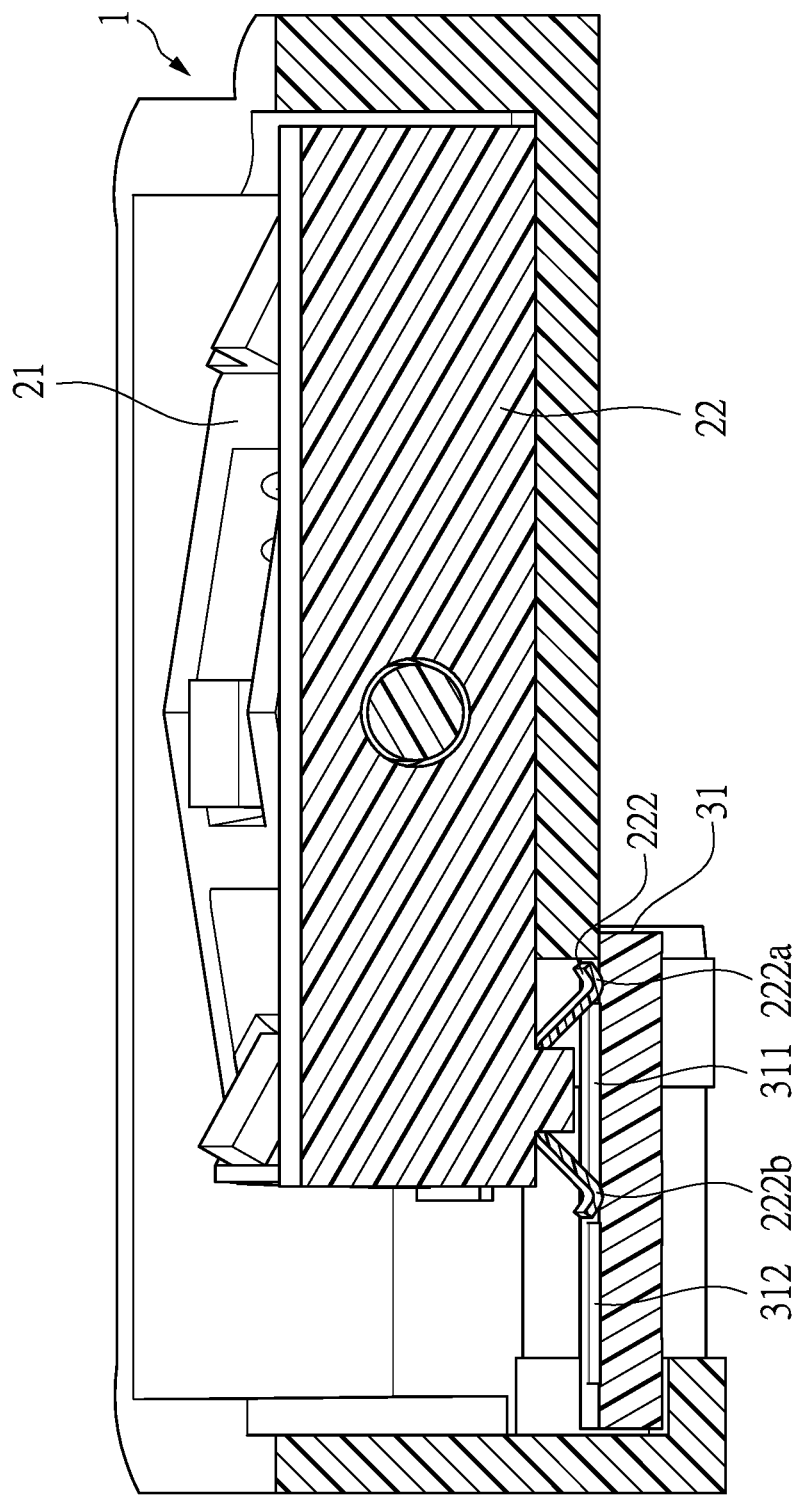
FIG. 4 shows a cross-sectional schematic view of the detecting device in the non-use state according to one of the embodiments of the instant disclosure.

Refer to FIG. 3 and FIG. 4. FIG. 3 shows a perspective assembly view of the detecting device in the non-use state according to one of the embodiments of the instant disclosure. FIG. 4 shows a cross-sectional schematic view of the detecting device in the non-use state according to one of the embodiments of the instant disclosure. The first plug hole and the second plug hole are shielded by the movable member 21 of the movable assembly in the non-use state of the socket. The pair of pin portions 222a, 222b of the conductive sheet 222 are crossed to the conductive pad 311. In other words, one of the pair of pin portions 222a contacts between two the conductive pads 311, 312, and other of the pair of pin portions 222b contacts between a lateral side of the circuit substrate 31 and the conductive pad 311. Then the circuit substrate 31 does not generate any detecting signal, and the processing unit determines the socket is in the non-use state.

In this embodiment, a distance between the pair of pin portions 222a, 222b of the conductive sheet 222 is equal to a length of the conductive pad 311. In another embodiment, the distance of the pair of pin portions 222a, 222b of the conductive sheet 222 is less than the length of the conductive pad 311. Thus the pair of pin portions 222a, 222b are simultaneously electrically contacted to the conductive pad 311 to short circuit the signal, and a short circuit signal is provided by the circuit substrate 31. The short circuit signal is inputted to the processing unit by the circuit substrate 31, and the processing unit determines the socket is in the non-use state.

Figure 5:
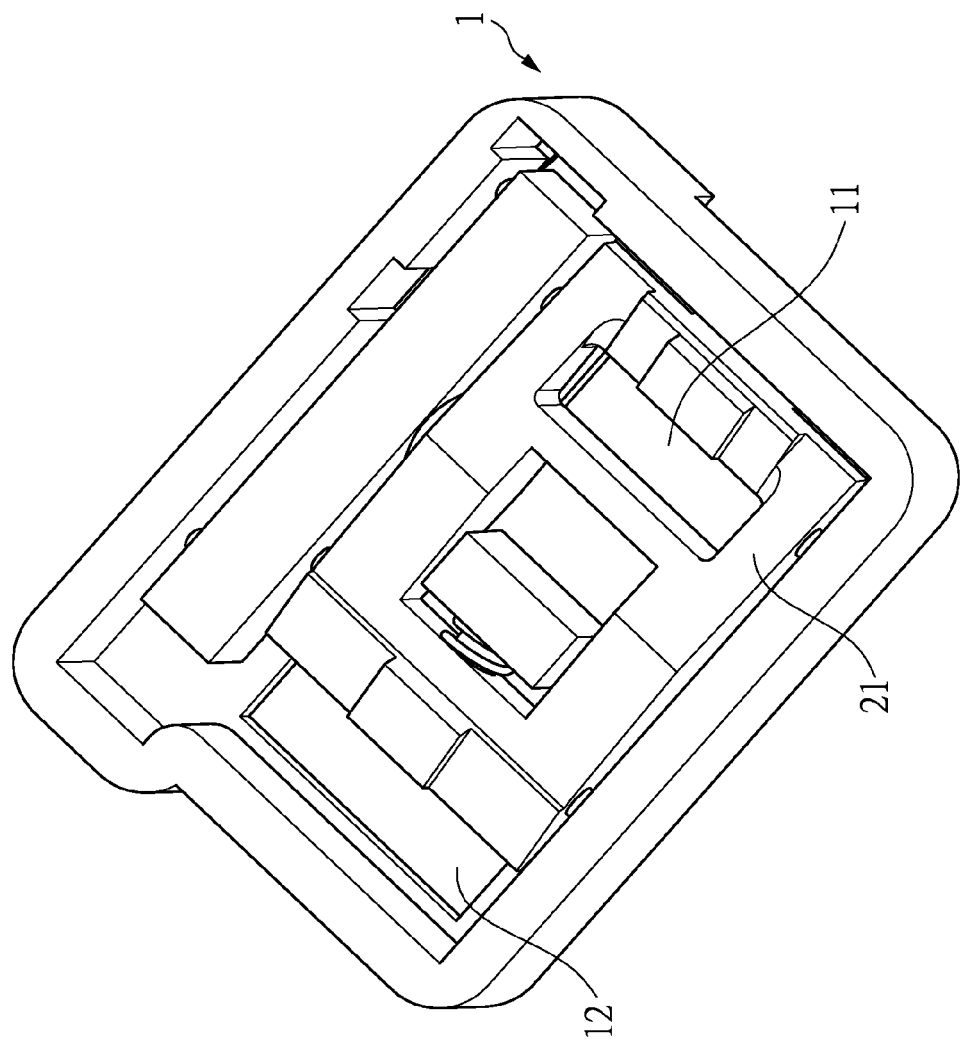
FIG. 5 shows a perspective assembly view of the detecting device in the use state according one of the embodiments of the instant disclosure.
Figure 6:
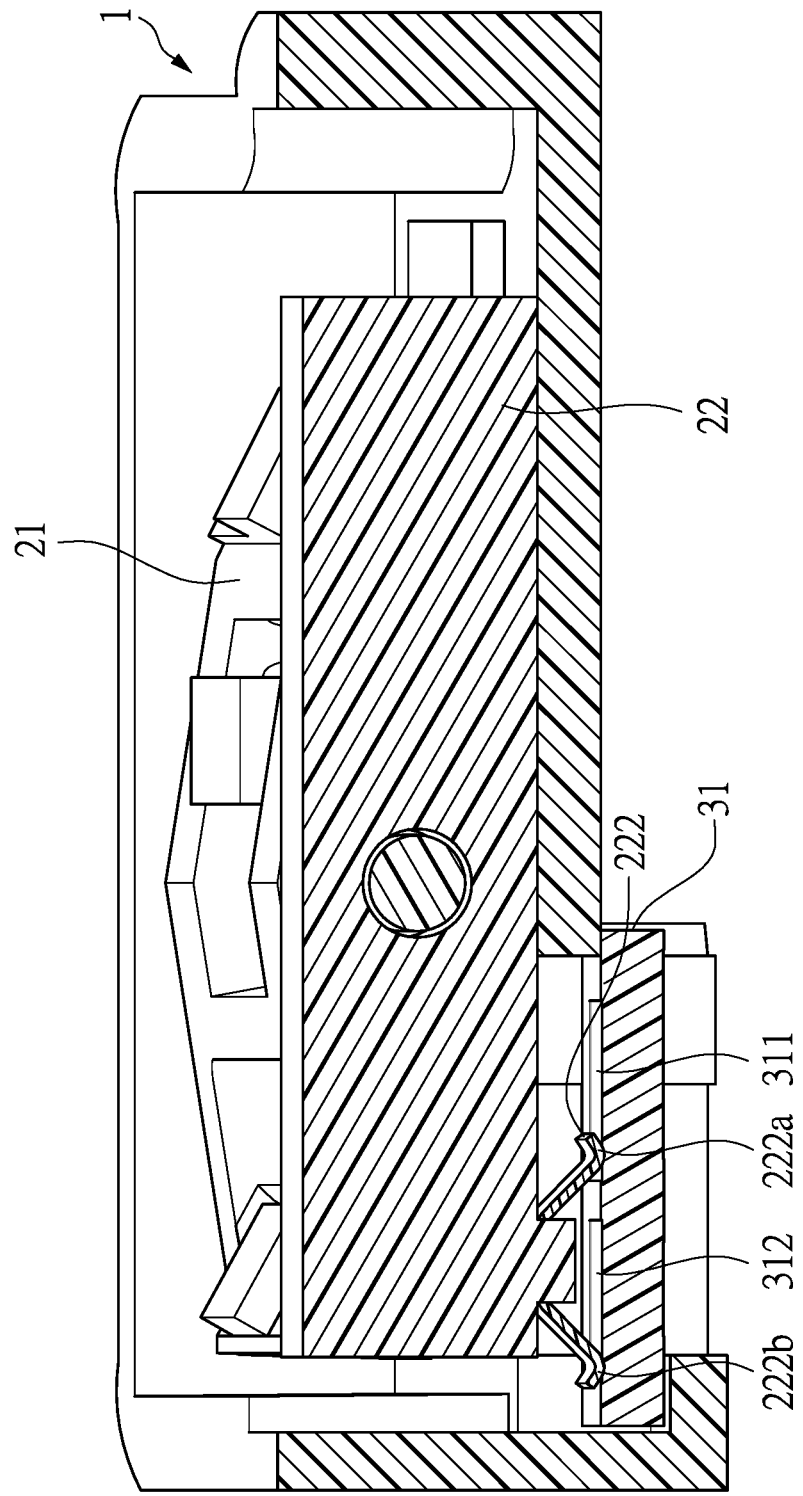
FIG. 6 shows a cross-sectional schematic view of the detecting device in the use state according to one of the embodiments of the instant disclosure.

Refer to FIG. 5 and FIG. 6. FIG. 5 shows a perspective assembly view of the detecting device in the use state according one of the embodiments of the instant disclosure. FIG. 6 shows a cross-sectional schematic view of the detecting device in the use state according to one of the embodiments of the instant disclosure. The first plug hole 11 and the second plug hole 12 are exposed by the movable member 21 of the movable assembly in the use state of the socket. The conductive sheet 222 of the connecting element 22 of the movable assembly is electrically connected to the conductive pads 311, 312, thus a detecting signal of the socket in-use is generated by the circuit substrate 31. When the movable member 21 is moved by an external pushing force (for example, a blades of a plug) the movable member 21 is moved to move the connecting element 22. The pair of pin portions 222a, 222b of the conductive sheet 222 on the connecting element 22 are respectively electrically contacted to two the conductive pads 311, 312. In other words, one of the pair of pin portions 222a is contacted to one of two the conductive pads 311, and the other of the pair of pin portions 222b is contacted to the other conductive pad 312. Then the circuit substrate 31 is turned on and generates a detecting signal to the processing unit, thus the processing unit determines the socket is in in-use state according to the detecting signal.

Figure 7:
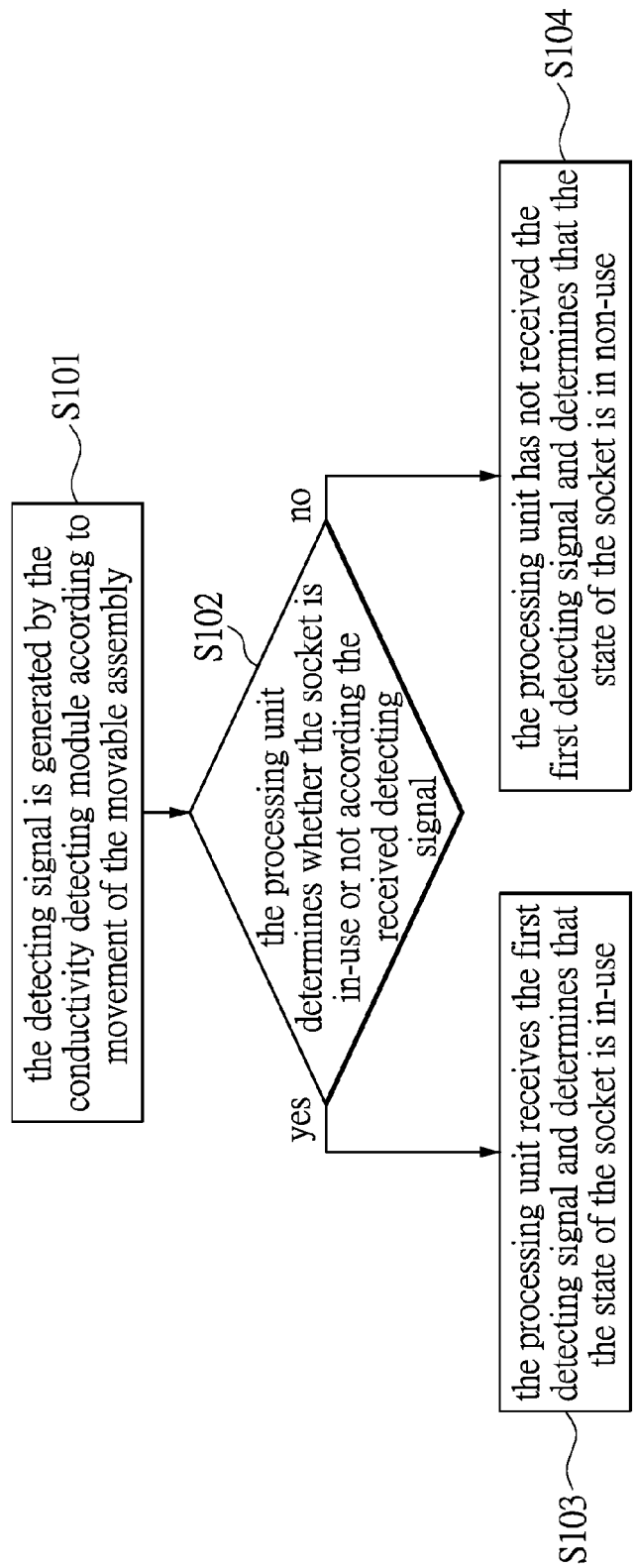
FIG. 7 shows a flow chart of a detecting method for detecting a usage state of a socket.

The flow chart of a detecting method of the detecting device for detecting a usage state of a socket Z will be described in detail as below. Refer to FIG. 4, FIG. 6 and FIG. 7. FIG. 7 shows a flow chart of a detecting method for detecting a usage state of a socket. The detecting device for detecting a usage state of a socket Z includes a carrier, a movable assembly and a conductivity detecting module. The carrier has a first plug hole and a second plug hole. The movable assembly is movably disposed in the carrier. The conductivity detecting module is disposed on the carrier. In the step S101, the detecting signal is generated by the conductivity detecting module according to movement of the movable assembly.

As shown in FIG. 4, the first hole and the second hole are shielded by the movable assembly when the movable assembly has not yet been moved by an external pushing force. A second detecting signal is generated by the conductivity detecting module according to the non-movement of the movable assembly. Because the movable assembly has not been moved yet, the pair of pin portions 222a, 222b of the conductive sheet 222 are crossed to the conductive pad 311, thus the circuit substrate 31 does not generate an electrical signal. The signal generating unit of the conductivity detecting module 3 does not receive any electrical signal from the circuit substrate 31, and the signal generating unit generates the second detecting signal to the processing unit.

As shown in FIG. 6, the first hole and the second hole are exposed according to movement of the movable assembly by an external pushing force. A first detecting signal is generated by the conductivity detecting module according to movement of the movable assembly. Because the movable assembly is moved by an external pushing force, one of the pair of pin portions 222a is electrically contacted to one of the conductive pads 311, and other of the pair of pin portions 222b is electrically contacted to the other conductive pads 312, and the circuit substrate 31 generates an electrical signal. The signal generating unit of the conductivity detecting module receives the electrical signal from the circuit substrate 31, and the signal generating unit generates the first detecting signal to the processing unit.

In the step S102, the processing unit determines whether the socket is in-use or not according the received detecting signal. In particular, the processing unit determines whether the received detecting signal is the first detecting signal. If the processing unit has received the first detecting signal, enter the step S103. Otherwise if the processing unit has not received the first detecting signal, enter the step S104.

In the step S103, the processing unit receives the first detecting signal and determines that the state of the socket is in-use. The first hole and the second hole are exposed by the movable assembly. Next, the processing unit generates a using signal to terminal equipment and notifies the user of the usage state of the socket.

In the step S104, the processing unit has not received the first detecting signal and determines that the state of the socket is in non-use. Specifically, the processing unit receives the second detecting signal. The first hole and the second hole are still shielded by the movable assembly.

Figure 8:
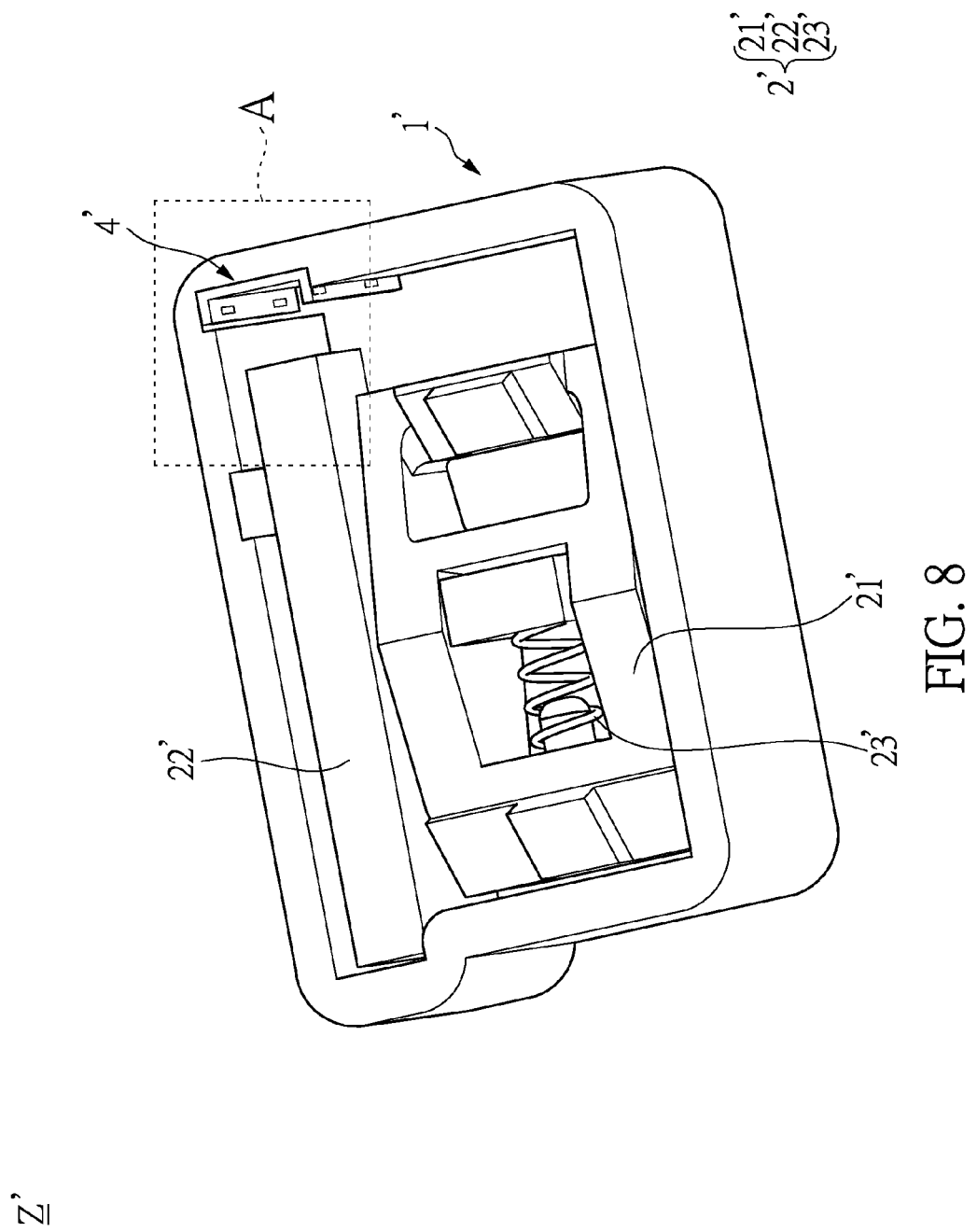
FIG. 8 shows a perspective view of the detecting device for detecting a usage state of a socket according to another embodiment of the instant disclosure.

Refer to FIG. 8. FIG. 8 shows a perspective view of the detecting device for detecting a usage state of a socket according to another embodiment of the instant disclosure. In this embodiment, a detecting device for detecting a usage state of a socket Z' is similar to the detecting device for detecting a usage state of a socket Z as shown in FIG. 1. The detecting device for detecting a usage state of a socket Z' comprises a carrier 1', a movable assembly 2' and a conductivity detecting module 4'. The position and connection of the carrier 1' and the movable assembly 2' is similar to the position and connection of the carrier 1 and the movable assembly 2 described above. However, the length of the connecting element 22' of the movable assembly 2' is larger than the movable member 21' when the connecting element 22' is mated with the movable member 21'. The following detailed description introduces the difference between the detecting device for detecting a usage state of a socket Z and the detecting device for detecting a usage state of a socket Z'.

Refer to FIG. 8. In this embodiment, the conductivity detecting module 4' is disposed on a groove of an internal wall of the carrier 1', and the conductivity detecting module 4' is correspondingly disposed to the connecting element 22'. In another embodiment, the conductivity detecting module 4' could be disposed in the mounting hole as described above or any position of the carrier 1'. The conductivity detecting module 4' should correspond to the movable assembly 2' for detecting a usage state of a socket Z, but the disposed position of the conductivity detecting module 4' is not limited herein.

Figure 9:
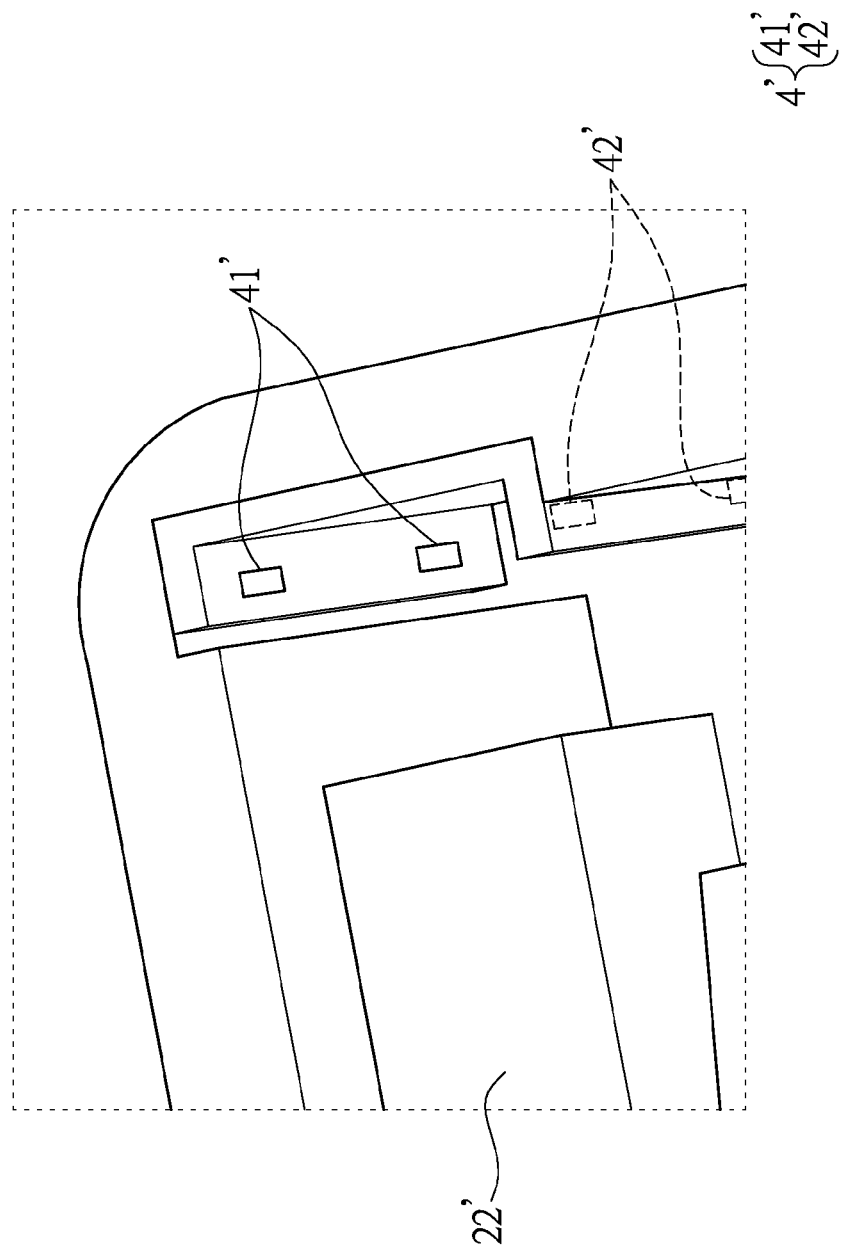
FIG. 9 shows an enlarged view of the detecting device in the use state according to another embodiment of the instant disclosure.

Refer to FIG. 8 and FIG. 9. FIG. 9 shows an enlarged view of the detecting device in the use state according to another embodiment of the instant disclosure. The conductivity detecting module 4' further includes a light generating unit 41' for generating a detecting light, and a light sensing unit 42' disposed opposite to the light generating unit 41' for receiving the detecting light. The light generating unit 41' for example an infrared ray emitting device or a light-emitting diode, it is not limited herein.

Figure 10:
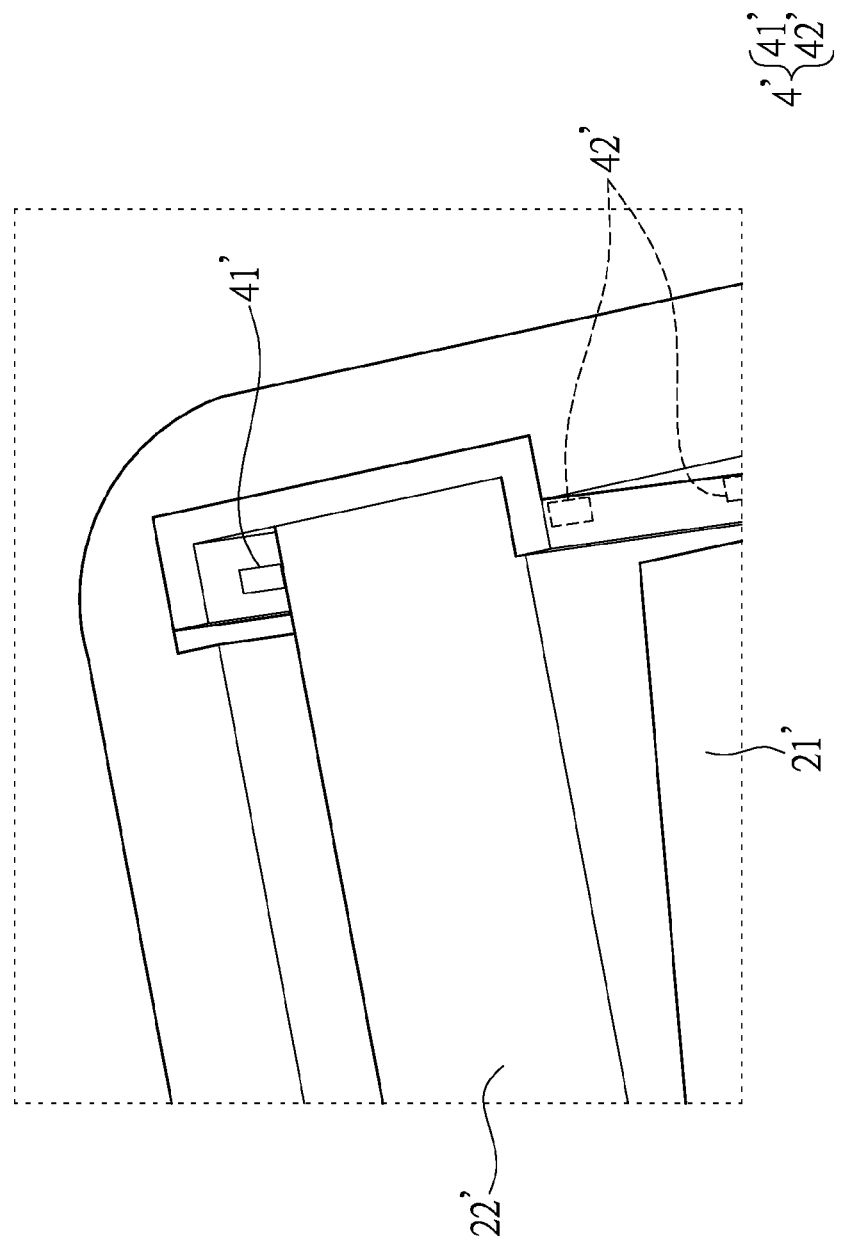
FIG. 10 shows an enlarged view of the detecting device in the non-use state according to another embodiment of the instant disclosure.

Refer to FIG. 7, FIG. 9 and FIG. 10. The flow chart of a detecting method as shown in FIG. 7 also can be described for the detecting device for detecting a usage state of a socket Z' of FIG. 8 to FIG. 10. The light generating unit 41' of the conductivity detecting module 4' continuously generates the detecting light to the light sensing unit 42'. A signal generating unit of the conductivity detecting module 4' receives a sensing signal. In the step S101, the detecting signal is generated by the conductivity detecting module 4' according to movement of the movable assembly.

As shown in FIG. 9, the first hole and the second hole are shielded by the movable assembly while the light generated according to the light generating unit 41' has not been shielded by the movable assembly, and a detecting signal generated by the light sensing unit 42' for the socket is for non-use. Because the movable assembly has not been moved yet by an external pushing force, the light generated by the light generating unit 41' is continuously detected by the light sensing unit 42'. The signal generating unit of the conductivity detecting module 4' receives the light signal generated by the light sensing unit 42', and the signal generating unit generates a second detecting signal to a processing unit.

As shown in FIG. 10, FIG. 10 shows an enlarged view of the detecting device in the non-use state according to another embodiment of the instant disclosure. The first hole and the second hole are exposed by the movable assembly while the light generated according to the light generating unit 41' has been shielded by the movable assembly, and a detecting signal is generated by the light sensing unit 42' when the socket is in-use. When the movable member 21' is moved by an external pushing force (for example, the blades of a plug), the movable member 21' is moved to move the connecting element 22'. The connecting element 22' shields the light generated by the light generating unit 41' and the light sensing unit 42' cannot sense any light. The signal generating unit of the conductivity detecting module 4' does not receive any signal generated from the light sensing unit 42', and the signal generating unit generates a first detecting signal to the processing unit.

In the step S102, the processing unit determines whether the socket is in-use or not according to the received detecting signal. Especially, the processing unit determines whether the received detecting signal is the first detecting signal. If the processing unit receives the first detecting signal, enter the step S103. Otherwise if the processing unit does not receive the first detecting signal, enter the step S104.

In the step S103, the processing unit receives the first detecting signal and determines the socket is in-use state. The first hole and the second hole are exposed by the movable assembly. Next, the processing unit generates a using signal to the terminal equipment and notifies the user of the usage state of the socket.

In the step S104, the processing unit has not received the first detecting signal and determines the socket is in the non-use state. Specifically, the processing unit receives the second detecting signal. The first hole and the second hole are still shielded by the movable assembly.

The descriptions illustrated supra set forth simply the preferred embodiments of the present invention; however, the characteristics of the present invention are by no means restricted thereto. All changes, alterations, or modifications conveniently considered by those skilled in the art are deemed to be encompassed within the scope of the present invention delineated by the following claims.

What is claimed is:

1. A detecting device for detecting a usage state of a socket, comprising:
    a carrier having a first plug hole and a second plug hole;
    a movable assembly movably disposed in the carrier; and
    a conductivity detecting module disposed on the carrier;
    wherein the movable assembly is moved for exposing the first plug hole and the second plug hole by an external pushing force, and a detecting signal of the socket in-use is generated by the conductivity detecting module according to movement of the movable assembly.

2. The detecting device for detecting a usage state of a socket according to claim 1, wherein the movable assembly includes a movable member movably disposed in the carrier and a connecting element mated with the movable member, and the movable member is moved for exposing the first plug hole and the second plug hole by the external pushing force, and a detecting signal of the socket in-use is generated by the conductivity detecting module according to movement of the movable member.

3. The detecting device for detecting a usage state of a socket according to claim 1, wherein the conductivity detecting module is disposed in a mounting hole on the carrier, and the conductivity detecting module further includes a circuit substrate and at least one conductive pad disposed on the circuit substrate.

4. The detecting device for detecting a usage state of a socket according to claim 3, wherein when the first plug hole and the second plug hole are exposed by the movable assembly, a conductive sheet disposed on the movable assembly is electrically connected to the conductive pad, thus the detecting signal of the socket in-use is generated by the circuit substrate.

5. The detecting device for detecting a usage state of a socket according to claim 1, wherein the conductivity detecting module further includes a light generating unit for generating a detecting light, and a light sensing unit disposed opposite to the light generating unit for receiving the detecting light.

6. The detecting device for detecting a usage state of a socket according to claim 5, wherein when the first plug hole and the second plug hole are exposed by the movable assembly, the detecting light generating from the light generating unit is shielded by the movable assembly, thus the detecting signal of the socket in-use is generated by the light sensing unit.

7. A detecting method for detecting a usage state of a socket, comprising the following steps:
    providing the socket, the socket including a carrier, a movable assembly movably disposed in the carrier and a conductivity detecting module disposed on the carrier, wherein the carrier has a first plug hole and a second plug hole;
    generating a detecting signal by the conductivity detecting module according to movement of the movable assembly; and
    determining whether the socket is in-use or not by a processing unit according to the detecting signal generated by the conductivity detecting module.

8. The detecting method for detecting a usage state of a socket according to claim 7, wherein the step of generating the detecting signal by the conductivity detecting module according to movement of the movable assembly further includes:
    exposing the first plug hole and the second plug hole and generating a first detecting signal by the conductivity detecting module according to movement of the movable assembly by an external pushing force.

9. The detecting method for detecting a usage state of a socket according to claim 8, wherein the step of determining whether the socket is in-use or not by the processing unit according to the detecting signal generated by the conductivity detecting module further includes:
    determining the socket is in-use by the processing unit according to the first detecting signal generated by the conductivity detecting module.

10. The detecting method for detecting a usage state of a socket according to claim 7, wherein the step of generating the detecting signal by the conductivity detecting module according to movement of the movable assembly further includes:
    shielding the first plug hole and the second plug hole and generating a second detecting signal while the movable assembly has not been moved yet by an external pushing force.

11. The detecting method for detecting a usage state of a socket according to claim 10, wherein the step of determining whether the socket is in use or not by the processing unit according to the detecting signal generated by the conductivity detecting module further includes:

determining the socket is in non-use state by the processing unit according to the second detecting signal generated by the conductivity detecting module.

\* \* \* \* \*